United States Patent
Darnold et al.

(10) Patent No.: US 11,369,534 B2
(45) Date of Patent: *Jun. 28, 2022

(54) SYSTEM AND METHOD FOR CUSHION INFLATION

(71) Applicant: ROHO, INC., Belleville, IL (US)

(72) Inventors: Leane Darnold, Kirkwood, MO (US); Kevin Meier, St. Louis, MO (US); Ross Peyton, St. Louis, MO (US); Glenn Fournie, Smithton, IL (US); Steve Steward, St. Louis, MO (US)

(73) Assignee: ROHO, INC., Belleville, IL (US)

( * ) Notice: Subject to any disclaimer, the term of this patent is extended or adjusted under 35 U.S.C. 154(b) by 189 days.

This patent is subject to a terminal disclaimer.

(21) Appl. No.: 16/075,071

(22) PCT Filed: Feb. 6, 2017

(86) PCT No.: PCT/US2017/016687
§ 371 (c)(1),
(2) Date: Aug. 2, 2018

(87) PCT Pub. No.: WO2017/136817
PCT Pub. Date: Aug. 10, 2017

(65) Prior Publication Data
US 2019/0029902 A1    Jan. 31, 2019

Related U.S. Application Data

(60) Provisional application No. 62/291,224, filed on Feb. 4, 2016, provisional application No. 62/291,342, filed on Feb. 4, 2016.

(51) Int. Cl.
*A61G 7/057* (2006.01)
*A61G 5/10* (2006.01)
(Continued)

(52) U.S. Cl.
CPC ........ *A61G 7/05769* (2013.01); *A47C 27/082* (2013.01); *A47C 27/083* (2013.01);
(Continued)

(58) Field of Classification Search
CPC ............ A61G 7/05769; A61G 7/05776; A61G 7/1021; A61G 13/1265; A61G 2203/20;
(Continued)

(56) References Cited

U.S. PATENT DOCUMENTS

| | | |
|---|---|---|
| 3,822,425 A | 7/1974 | Scales |
| 4,541,136 A | 9/1985 | Graebe |

(Continued)

FOREIGN PATENT DOCUMENTS

| | | |
|---|---|---|
| CN | 203688134 U | 7/2014 |
| WO | 2013010086 A2 | 1/2013 |

OTHER PUBLICATIONS

European Patent Office Extended Search Report for Application No. 17748337.7 dated Aug. 1, 2019 (7 pages).
(Continued)

*Primary Examiner* — Kevin F Murphy
*Assistant Examiner* — Jonathan J Waddy
(74) *Attorney, Agent, or Firm* — Michael Best & Friedrich LLP

(57) ABSTRACT

A system includes a client application executed by a client computing device for setting up an inflation level and checking an inflation level of an inflatable cushion having at least one air cell or zone and at least one pressure sensor within the cushion that detects air pressure. The client computing device communicates with the inflatable cushion and determines an optimal inflation level for a user of the inflatable cushion.

24 Claims, 14 Drawing Sheets

(51) Int. Cl.
*G16H 20/30* (2018.01)
*G16H 40/40* (2018.01)
*G16H 40/63* (2018.01)
*G01L 17/00* (2006.01)
*A47C 27/08* (2006.01)
*A47C 27/10* (2006.01)
*G05B 15/02* (2006.01)

(52) U.S. Cl.
CPC ............ *A47C 27/10* (2013.01); *A61G 5/1043* (2013.01); *A61G 5/1045* (2016.11); *A61G 5/1091* (2016.11); *A61G 7/05776* (2013.01); *G01L 17/00* (2013.01); *G16H 20/30* (2018.01); *G16H 40/40* (2018.01); *G16H 40/63* (2018.01); *A61G 2203/20* (2013.01); *A61G 2203/34* (2013.01); *G05B 15/02* (2013.01); *Y10T 137/3584* (2015.04); *Y10T 137/3662* (2015.04); *Y10T 137/3724* (2015.04); *Y10T 137/8326* (2015.04)

(58) Field of Classification Search
CPC .. A61G 5/1043; A61G 5/1045; A61G 5/1091; A61G 2203/34; A47C 27/082; A47C 27/083; A47C 27/10; G01L 17/00; Y10T 137/3584; Y10T 137/3662; Y10T 137/3724; Y10T 137/8326; G05B 15/02; G16H 20/30; G16H 40/40; G16H 40/63
See application file for complete search history.

(56) References Cited

U.S. PATENT DOCUMENTS

| | | | |
|---|---|---|---|
| 5,235,713 A * | 8/1993 | Guthrie | A61G 7/05769 5/411 |
| 6,415,814 B1 | 7/2002 | Hand et al. | |
| 7,414,536 B2 | 8/2008 | Call et al. | |
| 8,413,278 B2 * | 4/2013 | Chaffee | G05D 16/208 5/713 |
| 9,289,073 B2 * | 3/2016 | Chaffee | A47C 27/083 |
| 9,901,499 B2 * | 2/2018 | Darnold | A61G 7/05769 |
| 10,092,242 B2 * | 10/2018 | Nunn | A61B 5/6891 |
| 2003/0138329 A1 | 7/2003 | Koyano et al. | |
| 2003/0192125 A1 | 10/2003 | Graebe et al. | |
| 2005/0210993 A1 | 9/2005 | Toyoda et al. | |
| 2007/0227594 A1 * | 10/2007 | Chaffee | A47C 31/008 137/224 |
| 2010/0120362 A1 | 5/2010 | Walley et al. | |
| 2010/0170043 A1 * | 7/2010 | Young | A61B 5/4806 5/706 |
| 2011/0208541 A1 * | 8/2011 | Wilson | G06Q 50/22 705/3 |
| 2012/0105233 A1 | 5/2012 | Bobey et al. | |
| 2013/0284274 A1 | 10/2013 | Chaffee | |
| 2014/0007656 A1 | 1/2014 | Mahoney | |
| 2014/0047645 A1 | 2/2014 | Choi et al. | |
| 2014/0259430 A1 | 9/2014 | Rickman et al. | |
| 2014/0259434 A1 | 9/2014 | Nunn et al. | |
| 2015/0000044 A1 | 1/2015 | Morimura et al. | |
| 2015/0164236 A1 * | 6/2015 | Driscoll, Jr. | A47C 27/083 5/713 |
| 2016/0015184 A1 * | 1/2016 | Nunn | A47C 27/082 700/282 |
| 2016/0022521 A1 | 1/2016 | Darnold et al. | |
| 2016/0317370 A1 | 11/2016 | Evans et al. | |
| 2017/0239131 A1 | 8/2017 | Brzenchek et al. | |
| 2018/0280219 A1 | 10/2018 | Garrett et al. | |
| 2021/0307531 A1 * | 10/2021 | Lee | A47C 27/053 |

OTHER PUBLICATIONS

European Patent Office Extended Search Report for Application No. 17748339.3 dated Sep. 12, 2019 (5 pages).
United States Patent Office Action for U.S. Appl. No. 16/075,067 dated Sep. 18, 2019 (8 pages).
International Search Report and Written Opinion for Application No. PCT/US2017/016678 dated Jun. 9, 2017 (11 pages).
International Search Report and Written Opinion for Application No. PCT/US2017/016687 dated Apr. 21, 2017 (8 pages).

* cited by examiner

SYSTEM AND METHOD FOR CUSHION INFLATION

CROSS REFERENCE TO RELATED APPLICATIONS

This application is a national phase filing of International Patent Application No. PCT/US2017/016687, entitled "System and Method for Cushion Inflation" and filed on Feb. 6, 2017, which claims priority to U.S. Provisional Patent Application No. 62/291,224, entitled "System and Method for Cushion Inflation" and filed on Feb. 4, 2016, and to U.S. Provisional Patent Application No. 62/291,342, entitled "Valve Assembly for Cushion Inflation" and filed on Feb. 4, 2016, the entire contents of each application is herein incorporated by reference in its entirety. In addition, this application is related to U.S. application Ser. No. 14/435,812, filed Apr. 15, 2015, entitled "Cushion Immersion Sensor" and International Patent application No. PCT/US2014/066182, filed Nov. 18, 2014, entitled "Reduced Outflow Inflation Valve," that further claims priority to U.S. Provisional Patent Application No. 61/933,021 filed on Jan. 29, 2014, each of which is incorporated herein by reference in its entirety.

BACKGROUND

Air cell cushions are used by individuals who must remain seated for extended periods of time, for example, a disabled individual who uses a wheelchair for locomotion. Larger air cell cushions, generally configured as mattresses, are used by non-ambulatory or bed ridden individuals. Inflatable air cell cushions are employed to prevent pressure sores on the buttocks or at other bony prominences. These air cell cushions provide support, while distributing weight, generally uniformly through a multiplicity of interconnected air cells.

The typical air cell cushion includes a base and an array of interconnected, upstanding individual air cells, usually arranged in transverse and longitudinal rows. An air inflation tube is in fluid communication with one of the cells. The inflation tube includes a screw type valve. The air cell cushion generally has a stretchy cover. A representative embodiment of such an air cell is disclosed in U.S. Pat. No. 4,541,136, which is incorporated herein by reference.

For proper seating on the cushion, the cushion is placed on a relatively firm or hard surface, such as a wheel chair seat or other type of seat or chair. The cushion also may be used with a sling seat wheelchair having a hammock-type fabric surface. The individual or caregiver (e.g., user) opens the valve and pumps air into the cushion until it is well inflated. The user then sits on the cushion and air is released through the valve until the user is optimally immersed in the air cell cushion. The valve is then closed. Proper immersion optimizes weight distribution and minimizes peak pressures on the anatomy.

Conventionally, proper immersion has been determined by a hand check method. The user inserts a hand between the body and cushion to determine when the user is properly immersed in the cushion. This is a subjective measurement and the depth of immersion can vary depending on who is checking immersion depth. Thus, it is prone to inaccurate measurement and error.

Computing devices have gradually become ubiquitous and a part of daily life. Users of smartphones and tablets have access to a portable device that is capable of communicating with others, capable of executing applications, and capable of sending information to other devices and receiving information from other devices.

It is with these issues in mind, among others, that various aspects of the disclosure were conceived.

SUMMARY

According to one aspect, an inflation system for inflating a cushion includes a client computing device that is in communication with the cushion, the client computing device having at least one processor to execute an application that obtains inflation information from the cushion and determines an appropriate inflation level for inflating at least one inflation zone of the cushion that provides an optimal immersion depth for a user of the cushion. In an exemplary embodiment, the client computing device is a smartphone or tablet that communicates wirelessly with the cushion via a Bluetooth network or another personal area network. The inflatable cushion may be easily setup for use by a user and easily checked to ensure that the cushion is appropriately inflated in order to prevent pressure sores and ulcers.

According to one embodiment, a system includes one or more processors to transmit a first communication to a hardware device associated with an inflatable cushion to configure the cushion, the first communication comprising instructions to set an inflation level for at least one inflation zone of the cushion, receive a second communication from the hardware device associated with the inflatable cushion, the second communication comprising real-time information associated with the inflation level for the at least one inflation zone of the cushion, display on a user interface the real-time information associated with the inflation level for the at least one inflation zone of the cushion, determine an appropriate inflation level for the at least one inflation zone of the cushion based on the second communication, and transmit a third communication to the hardware device to store the inflation level for the at least one inflation zone of the cushion after determining the appropriate inflation level for the at least one inflation zone of the cushion.

According to a further embodiment, a method includes transmitting, by at least one processor, a first communication to a hardware device associated with an inflatable cushion to configure the cushion, the first communication comprising instructions to set an inflation level for at least one inflation zone of the cushion, receiving, by the at least one processor, a second communication from the hardware device associated with the inflatable cushion, the second communication comprising real-time information associated with the inflation level for the at least one inflation zone of the cushion, displaying, by the at least one processor, on a user interface the real-time information associated with the inflation level for the at least one inflation zone of the cushion, determining, by the at least one processor, an appropriate inflation level for the at least one inflation zone of the cushion based on the second communication, and transmitting, by the at least one processor, a third communication to the hardware device to store the inflation level for the at least one inflation zone of the cushion after determining the appropriate inflation level for the at least one inflation zone of the cushion.

According to another embodiment, a non-transitory computer-readable medium includes instructions stored thereon that, when executed by one or more processors, cause the one or more processors to perform operations including transmitting a first communication to a hardware device associated with an inflatable cushion to configure the cushion, the first communication comprising instructions to set an inflation level for at least one inflation zone of the cushion, receiving a second communication from the hardware device associated with the inflatable cushion, the second communication comprising real-time information associated with the inflation level for the at least one inflation zone of the cushion, displaying on a user interface the real-time information associated with the inflation level for the at least one inflation zone of the cushion, determining an appropriate inflation level for the at least one inflation zone of the cushion based on the second communication, and transmitting a third communication to the hardware device to store the inflation level for the at least one inflation zone of the cushion after determining the appropriate inflation level for the at least one inflation zone of the cushion.

These and other aspects, features, and benefits of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment.

DETAILED DESCRIPTION

Figure 1:
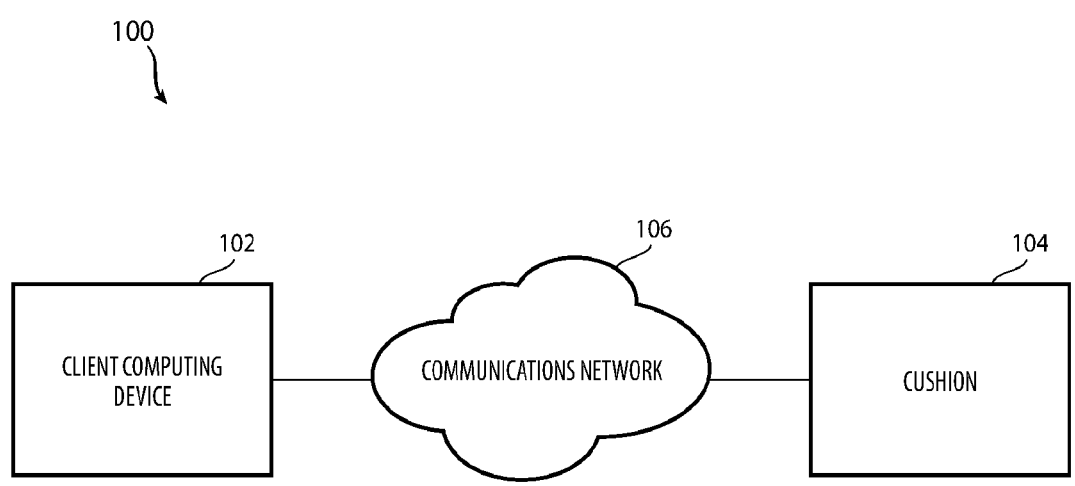
FIG. 1 is a block diagram of an inflation system according to an example embodiment.

For the purpose of promoting an understanding of the principles of the present disclosure, reference will now be made to the embodiments illustrated in the drawings, and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates.

Aspects of a system and method for inflation provide a client application executed by a client computing device for determining an appropriate inflation level of an inflatable cushion having at least one air cell or zone and at least one pressure sensor within the cushion that detects air pressure. The client computing device communicates with the inflatable cushion, obtains pressure information from the pressure sensor, and determines an inflation level for a user of the inflatable cushion.

In one embodiment, a user inflates the cushion using a hand pump, positions their body on the cushion, and the client application determines whether the inflation level is correct for the user. The client application may provide feedback indicating whether the inflation level is appropriate, too high, or too low. In another embodiment, the cushion automatically inflates, the user positions their body on the cushion, and the client application determines whether the inflation level is correct for the user.

The client application wirelessly communicates with the cushion and detects optimal immersion of a cushion user into the cushion. The immersion depth of the user positioned on the cushion is determined by the client application by sensing air pressure in the cushion. The client application accurately determines changes in air pressure as air exits the cushion, which allows the client application to determine the optimal internal cushion pressure for the user. The client application may be executed by a smartphone or a tablet and provides a touch-based user interface that allows a user to easily set up the cushion for use and check the air pressure within the cushion.

The user interface allows a user to sit on the cushion, use a touch-based user interface of the application, and start an automated process or partially automated process that detects the optimal immersion for the user into the cushion. The user may attach a hand pump or an automated air pump to the cushion that inflates the cushion. The cushion may be overfilled with air. Then, the user may sit on the cushion. During the process, the client application executed by the smartphone or the tablet performs an algorithm that includes setting an optimal inflation level for at least one inflation zone of the cushion.

The client application sets the inflation level for at least one inflation zone of the cushion by determining an air pressure level within the cushion at a particular time interval over a period of N time, determining an average pressure level over the period of N time, determining a difference in the air pressure level minus the average pressure level over the N period of time, and determining that the difference is less than a predetermined value when the appropriate inflation level and an optimal immersion has been reached. When the client application determines that the difference is less than a predetermined value, the optimal immersion for the user has been reached. At this point, the smartphone or tablet stores information associated with the optimal immersion and the inflation level for the at least one inflation zone of the cushion in memory of the smartphone or tablet and/or in memory of the cushion. As an example, the smartphone or tablet may store the inflation level for each separate zone of the cushion in memory of the smartphone or tablet and/or in memory of the cushion. The user may lock the air in each of the separate zones so that stability and positioning are maintained as the user uses the cushion. In addition, the appropriate air pressure in each separate zone may be recalled from memory of the smartphone or tablet and/or the memory of the cushion during a check process.

Additionally, after the setup of the cushion for the user, the client application allows the user to easily check that the optimal immersion and the inflation level for the at least one inflation zone of the cushion is correct. The client application may automatically perform checks periodically, such as a few times a day while the user is immersed in the cushion or upon an explicit request of the user when the user makes a request within the client application. The user interface of the client application may display information associated with the inflation level for the at least one inflation zone of the cushion to the user and indicate the inflation level for each inflation zone of the cushion. The user interface may indicate that the inflation level for each inflation zone of the cushion is too high, too low, or appropriate. In addition, the user interface may provide historical information associated with the inflation level for each inflation zone of the cushion so that the user can view the inflation level for the cushion over a period of time, such as a previous month. The user interface may allow the user to send this historical information to a caregiver, a clinician, or another recipient.

One smartphone or tablet with the client application may be used to setup multiple cushions for multiple users. This may allow the caregiver, the clinician, or other person to setup, inflate, and check the cushions for the multiple users. The smartphone or tablet with the client application may connect to a first cushion to setup, inflate, and check the first cushion for a first user. Then, the smartphone or tablet with the client application may disconnect from the first cushion to setup, inflate, and check a second cushion for a second user. Then the smartphone or tablet with the client application may disconnect from the second cushion to setup, inflate, and check a third cushion for a third user, and so on. The smartphone or tablet with the client application may be used to check and monitor each of the cushions for the users at a particular time each day or at another interval of time. In one example, the smartphone or tablet may receive a reminder to check the first cushion at 1:00 pm each day, a reminder to check the second cushion at 2:00 pm each day, and a reminder to check the third cushion at 3:00 pm each day. The smartphone or tablet may receive a reminder in the form of a notification to check the cushion. The notification may be used to launch the client application and check the cushion.

FIG. 1 shows a block diagram of an inflation system 100 according to an example embodiment. According to an aspect of the present disclosure, the inflation system 100 includes a client computing device 102 and at least one inflatable cushion 104. The cushion 104 may include an embedded computing device and may have at least one inflation zone, segment, portion, section, compartment, or division. As an example, the cushion 104 may be divided into inflatable quadrants. The embedded computing device may be removable from the cushion 104 and/or may be permanently attached to the cushion 104. The cushion may be cleaned when the embedded computing device is permanently attached to the cushion 104 or if the embedded computing device is removable from the cushion 104.

Although described as an inflatable cushion, the cushion may be any type or size of cushion, inflatable mattress, seating, or bedding. The client computing device 102 and/or the cushion may be powered by a battery such as a rechargeable battery and/or may be powered via a conventional alternating current (AC) power supply. Alternatively, the client computing device 102 and/or the cushion 104 may be powered by solar energy and/or another power supply.

The client computing device 102 and the cushion 104 communicate and coordinate their actions by passing messages over a communication network 106. The communication network 106 can be one or more of the Internet, an intranet, a personal area network (PAN) such as a Bluetooth network, a cellular communications network, a WiFi network, a packet network, or another wired and/or wireless communication network or a combination of any of the foregoing. As an example, the one or more computing devices communicate data in packets, messages, or other communications using a common protocol, e.g., Bluetooth, Hypertext Transfer Protocol (HTTP) and/or Hypertext Transfer Protocol Secure (HTTPS). As an example, the inflation system 100 may be a cloud-based computer system or a distributed computer system.

The client computing device 102 may be a Bluetooth Low Energy (BLE, Bluetooth LE, Bluetooth Smart) device based on the Bluetooth 4.0 specification or another specification. The cushion 104 may also be a Bluetooth Low Energy (BLE, Bluetooth LE, Bluetooth Smart) device based on the Bluetooth 4.0 specification or another specification. According to an example embodiment, the client computing device 102 and the cushion 104 are paired and communicate wirelessly using a short range wireless network, e.g., Bluetooth (IEEE Standard 802.15). The short range wireless network may be a wireless personal area network (WPAN). In one example, the user may press a hardware button and/or a software button of the cushion 104 to begin pairing the cushion with the client computing device 102. A light emitting diode (LED) associated with the cushion may begin to blink when the pairing begins. After selecting a pairing button in a user interface of the client computing device 102, the LED may solidly illuminate rather than blink. After the cushion and the client computing device 102 are paired, the LED may no longer be illuminated.

In one embodiment, one or more cushions 104 may be paired with a single client computing device 102. A caregiver may pair one or more cushions for users, inflate the one or more cushions for the users, and check the inflation level of the one or more cushions using a single client computing device 102. The computing device 102 may connect to each cushion one at a time to inflate the cushion and check the inflation level of the cushion 104. When the client computing device 102 first pairs with the cushion, the client computing device 102 may prompt the user for a serial number of the cushion and the user may be asked to create a PIN number or a password. If the user creates a PIN number or a password, then the client computing device 102 may not connect to the cushion 104 unless the user provides a correct PIN number or a correct password.

In another example, the client computing device 102 and/or the cushion 104 may create a personal area network and/or a mesh network for communicating. Additionally, the client computing device 102 and the cushion 104 may communicate using Zigbee, Wi-Fi, near field magnetic inductance, sonic (sound) waves, and/or infrared (light) waves, among others.

The cushion 104 may be an air cell cushion including a base and an array of interconnected, upstanding individual air cells, usually arranged in transverse and longitudinal rows. An air inflation tube may be in fluid communication with one of the cells. The inflation tube may include a screw type valve. This screw type valve may be connected to a hand pump or an automatic pump for inflation and/or deflation. To inflate/deflate the cushion 104, the user may open the valve. After the cushion 104 is inflated, the valve may be closed. The air cells are in fluid communication through air channels formed in the base so that air introduced into the cushion 104 flows into all the cells until the air pressure is equalized among the cells. A representative embodiment of such an air cell is disclosed in U.S. Pat. No. 4,541,136, which is incorporated herein by reference.

The client computing device 102 may be used with any type of inflatable cushion or mattress, whether employing a plurality of individual air cells or fewer air filled compartments or bladders or a single bladder. As another embodiment, the client computing device 102 may be used with zoned cushions having at least one zone or a plurality of inflation zones wherein the air cells are divided into the plurality of zones. As a further embodiment, the client computing device 102 may be used with segmented cushions having at least one segment or a plurality of segments wherein the air cells are divided into the plurality of segments.

In an exemplary embodiment, the cushion 104 comprises a hardware device such as a dedicated electronic device having a processor and memory. In addition, the hardware device comprises a Bluetooth transceiver for communicating with the client computing device 102. The hardware device may further include one or more pressure transducers that determine air pressure within the cushion 104. As an example, the pressure transducers may detect 0-100 mmHg in 0.25 mmHg increments.

Figure 2:
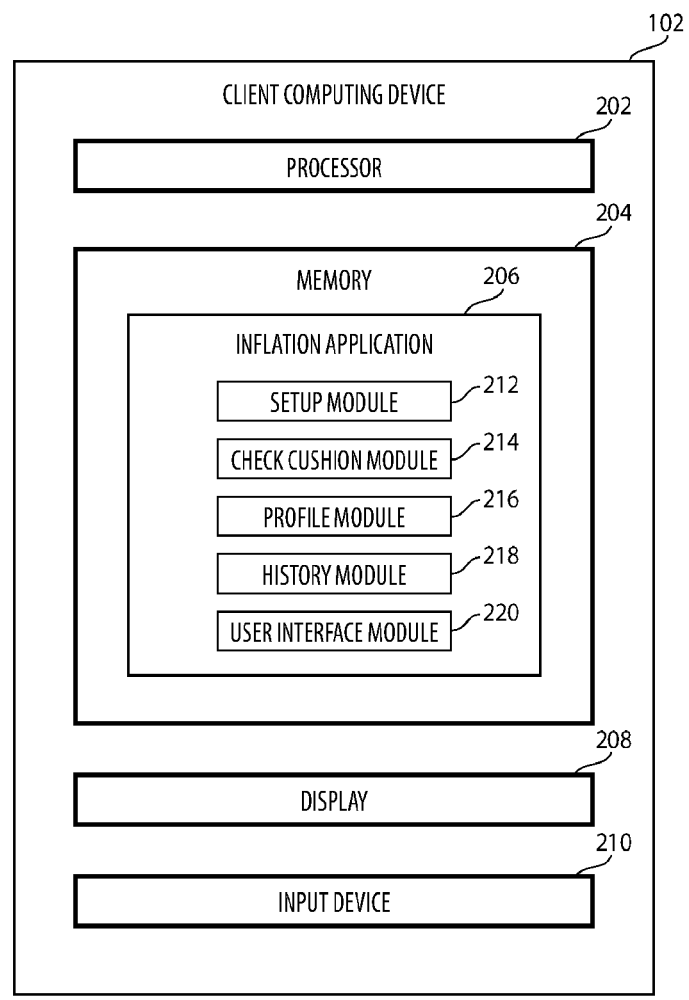
FIG. 2 is a block diagram of a client computing device according to an example embodiment.

FIGS. 1 and 2 illustrate a block diagram of the client computing device 102 according to an example embodiment. The client computing device 102 may be a computer having a processor 202 and memory 204, such as a laptop, desktop, tablet computer, mobile computing device (e.g., a smartphone), a wearable device, or a dedicated electronic device having a processor and memory. The one or more processors 202 process machine/computer-readable executable instructions and data, and the memory 204 stores machine/computer-readable executable instructions and data including one or more applications, including an inflation application 206. The processor 202 may include and/or may be in communication with one or more hardware devices including a Bluetooth transceiver for transmitting messages to the cushion and receiving messages from the cushion 104. The processor 202 and memory 204 are hardware. The memory 204 includes random access memory (RAM) and non-transitory memory, e.g., a non-transitory computer-readable storage medium such as one or more flash storages or hard drives. The non-transitory memory may include any tangible computer-readable medium including, for example, magnetic and/or optical disks, flash drives, and the like. Additionally, the memory 204 may also include a dedicated file server having one or more dedicated processors, random access memory (RAM), a Redundant Array of Inexpensive/Independent Disks (RAID) hard drive configuration, and an Ethernet interface or other communication interface, among other components.

The inflation application 206 of the client computing device 102 provides a client user interface that provides cushion setup for one or more users, communicates with the cushion 104 to optimally inflate the cushion 104 to an appropriate level and optimally immerse the user in the cushion 104, displays inflation information associated with the cushion 104, and stores inflation information associated with the one or more users. The inflation application 206 may be a component of an application and/or service executable by the client computing device 102. For example, the inflation application 206 may be a single unit of deployable executable code. According to one aspect, the inflation application 206 may be a web application, a native application, and/or a mobile application (e.g., an app) downloaded from a digital distribution application platform that allows users to browse and download applications developed with mobile software development kits (SDKs) including the App Store and GOOGLE PLAY®, among others. The inflation application 206 may be installed on the client computing device 102, which may have the iOS operating system or an ANDROID™ operating system, among other operating systems.

The client computing device 102 receives messages from the cushion 104 and sends responses, e.g., Bluetooth messages and corresponding Bluetooth responses. The responses may comprise requested content. As an example, the client computing device 102 may send a message to the cushion 104 requesting that the cushion inflation level be adjusted to an optimal immersion level for a particular user. The cushion 104 receives the message, generates a response, and transmits the response to the client computing device 102.

The client computing device 102 further includes a display 208 and an input device 210. The display 208 is used to display visual components of the inflation application 206, such as at a user interface including a native application interface and/or a web browser interface. In one example, the user interface may display a user interface of the inflation application 206. The display 208 can include a cathode-ray tube display, a liquid-crystal display, a light-emitting diode display, a touch screen display, and other displays. The input device 210 is used to interact with the inflation application 206 or otherwise provide inputs to the client computing device 102 and may include a mouse, a keyboard, a trackpad, and/or the like. The input device 210 may be included within the display 208 if the display is a touch screen display. The input device 210 allows a user of the client computing device 102 to manipulate the user interface of the inflation application 206 or otherwise provide inputs.

The input device 210 may further include a camera, among other input devices, in communication with or connected to the client computing device 102.

FIG. 2 illustrates a block diagram of the inflation application 206 of the client computing device 102 according to an example embodiment. The client computing device 102 includes computer readable media (CRM) in memory 204 on which the inflation application 206 is stored. The computer readable media may include volatile media, nonvolatile media, removable media, non-removable media, and/or another available medium that can be accessed by the processor 202. By way of example and not limitation, the computer readable media comprises computer storage media and communication media. Computer storage media includes non-transitory storage memory, volatile media, nonvolatile media, removable media, and/or non-removable media implemented in a method or technology for storage of information, such as computer/machine-readable/executable instructions, data structures, program modules, or other data. Communication media may embody computer/machine-readable/executable instructions, data structures, program modules, or other data and include an information delivery media or system, both of which are hardware.

Figure 2A:
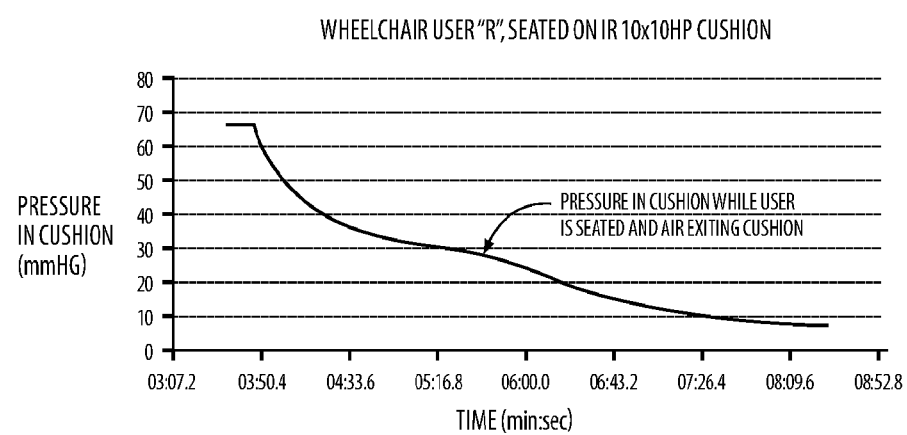
FIG. 2A illustrates a graph associated with the determination of optimal immersion pressure of a seated user.

The inflation application 206 includes a setup module 212 that executes an algorithm for detecting optimal immersion of the cushion user into the inflatable cushion. The immersion depth of the user positioned on the cushion 104 is determined by sensing air pressure in the cushion 104. The pressure transducer of the cushion 104 senses the air pressure and transmits information associated with the air pressure via Bluetooth to the client computing device 102. The setup module 212 accurately determines changes in pressure as air exits the cushion, which allows the setup module 212 to determine the optimal internal cushion pressure for the user. In an exemplary embodiment, the setup module 212 obtains pressure readings from the cushion 104 at a particular interval of time, e.g., once per second. The setup module 212 determines an average pressure over a period of N time. As an example, the average pressure may be determined over a period of six to ten seconds. The setup module 212 determines continuous average pressure readings and determines a difference in a current average pressure reading minus the average pressure over the preceding N period of time. When the difference is less than a predetermined value, then the slope of the pressure curve indicates that an optimal pressure representing ideal or optimal immersion for the user has been reached. An example of a pressure curve for a user R is shown in FIG. 2A. The area of optimal immersion for the user R is indicated within circle 230 in FIG. 2B.

Figure 2B:
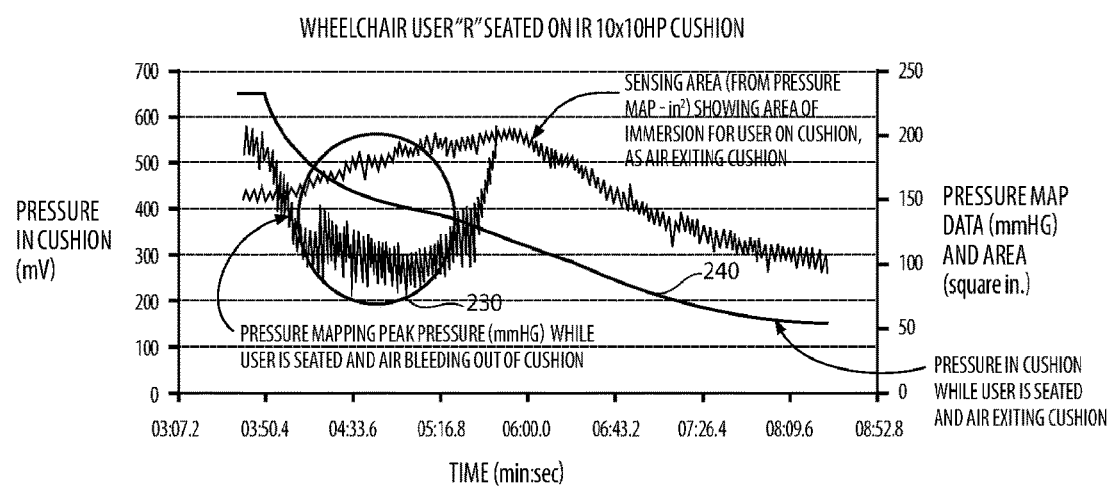
FIG. 2B illustrates a graph that shows the relationship between pressure mapping and optimal immersion pressure of the seated user.

The absolute value of air pressure in the cushion 104 may differ depending on a volume of air in a particular cushion, the surface area of the user contacting the cushion, and the weight of the user. As shown in FIG. 2B, optimal area is not a finite point, but may represent a discrete continuum along the curve.

This determination of the optimal pressure representing ideal or optimal immersion may be based on the following exemplary source code:

```
var CurrentAvg =
   PressureReadings.GetRange(PressureReadings.Count -
8, 8).ToList( ).Select(o => o.Pressures.Average( )).ToList( ).Average( );
   var LastAvg =
PressureReadings.GetRange(PressureReadings.Count -
MINIMUM_CHECKS, 8).ToList( ).Select(o =>
o.Pressures.Average( )).ToList( ).Average
( );
AverageReading = Math.Abs(LastAvg - CurrentAvg);
```

First, the setup module 212 determines the average pressure over a period of N time. As shown here, the average is based on eight readings from the pressure transducers of the cushion 104. Next, the setup module 212 obtains the average pressure from five seconds ago. Then, the setup module 212 determines the absolute value of the slope between the current average pressure and average pressure from five seconds ago.

The setup module 212 may send instructions to the cushion to store the inflation level for the at least one inflation zone of the cushion 104 in memory of the cushion 104. The instructions may include determining an air pressure level within the cushion 104 at a particular time interval over a period of N time, determining an average pressure level over the period of N time, determining a difference in the air pressure level minus the average pressure level over the N period of time, and determining that the difference is less than a predetermined value when the appropriate inflation level and an optimal immersion has been reached.

Example user interfaces associated with the setup module 212 are shown in FIGS. 4-11. For example, when the optimal immersion is reached, the user interface of the inflation application 206 may indicate with an indication on the display 208. Such an indication may be a check mark or another type of indication that indicates that the immersion is at an optimal level. At this point, the user may shut the valve of the cushion 104 if the valve is manually opened. The inflation application 206 may provide adequate time to allow the user to close the valve and still remain at the optimal immersion. As an example, the user may be given ten to fifteen seconds to close the valve. If the user waits too long and too much air is released, then the inflation application 206 may display an indication on the display that indicates that the cushion is underinflated. Such an indication may be an "X" or another type of indication such as a "−". This indication is a "too low" indicator. If the user does not release enough air, the inflation application 206 may provide an indication on the display 208 that indicates that the cushion is overinflated. Such an indication may be an "X" or another type of indication such as "+". This indication is a "too high" indicator.

During set up, the setup module 212 may determine that the user is not seated on the cushion 104. The setup module 212 may determine that the optimal immersion would be extremely low and the setup module 212 may not operate without the user seated on the cushion 104. Hence, the user should be positioned on the cushion 104 to establish the appropriate inflation level for the user.

FIG. 2B illustrates the validity of results determined by the client computing device 102. The data shown in FIG. 2B represents pressure readings obtained every second as air is released from the cushion 104. Graphed internal pressure 240 decreases rapidly as air is first released from the cushion 104 when the user is sitting on it. The ideal or optimal immersion of the user is in the area indicated by 230. This area 230 is used to determine the appropriate predetermined value of the difference between the average pressure level minus the average pressure level over the N period of time. The graphed line 240 illustrates the pressure mapping peak values for the user in relation to the internal cushion pressure. As shown, the graphed pressure mapping peak value 240 increases rapidly outside the ideal immersion of the user area shown in 230. The sensing area (which is the user contacted area with the cushion obtained by pressure mapping) changes as the user is immersed into the cushion. Outside the optimal immersion range 230, the sensing area may drop off sharply when the user is not properly supported by the inflated cushion 104.

As may be appreciated, the client computing device 102 may indicate optimal immersion based upon internal cushion pressure for any type or size of cushion and for users of various sizes and shapes. Once the optimal immersion pressure is determined, it is stored in the memory 204 of the client computing device 102 and/or the memory of the cushion 104. This optimal immersion pressure may be reset if there are significant changes in the size of the user or weight or physiological condition.

The client computing device 102 and/or the cushion 104 may emit an audible alarm that provides a warning signal if there is a change of user immersion depth and internal pressure. Different audible alarms may be provided to indicate different functions or readings, for example, under inflation, over inflation, optimal immersion, or low battery of the cushion. As another example, the client computing device 102 may provide a notification that includes a visual, audible, and/or haptic notification associated with the under inflation, over inflation, optimal immersion, or low battery of the cushion 104. The notification may be a push notification or another type of notification such as a text message or a media message.

The setup module 212 determines a specific or quantifiable internal pressure within the cushion 104 that reflects optimal immersion of a specific user of the cushion. This is significant because the quantifiable internal pressure for proper immersion of different users may vary, depending upon the cushion volume, user's body weight, body morphology, and the internal volume of the cushion.

The inflation application 206 further includes a check cushion module 214 that determines whether any adjustments should be made to the inflation of the cushion and immersion of the user by comparing at least one current cushion pressure level with at least one appropriate saved pressure level as determined by the setup module 212. The check cushion module 214 may execute once a day or a number of times a day automatically at particular and/or random times that may be selected by the user and store information associated with the comparison in the memory 204. In another embodiment, the check cushion module 214 may be executed upon a request by the user to check the cushion and compare the current inflation level with the optimal inflation level for the user. Example user interfaces associated with the check cushion module 214 are shown in FIGS. 4-11.

As the check cushion module 214 makes checks of immersion status, the client computing device 102 and/or the cushion 104 retrieves a range of acceptable high/low values around optimal immersion pressure that were stored in memory 204 of the client computing device 102 and/or memory of the cushion. As long as the pressure in the cushion 104 is within this established range for this user, the client application 206 may display on the display 208 an indication that indicates that the cushion 104 is at the appropriate inflation level.

In one embodiment, the check cushion module 214 transmits a first communication to the cushion 104 that includes a current date and a request to retrieve a current pressure level and previous stored pressure levels. The check cushion 214 may determine what historical pressure levels are not present in the memory 204 of the client computing device 102 and the request may include a request for the missing historical pressure levels. The check cushion module 214 may communicate with the user interface module 220 to display a current status of the cushion 104 and provide information regarding history of previous checks performed by the check cushion module 214.

The inflation application 206 further includes a profile module 216 that receives information about the user and stores the information about the user in the memory 204. As an example, when setting up the cushion 104 for use by the user and before detecting optimal immersion of the cushion user into the inflatable cushion, the profile module 216 may request information about the user. The profile module 216 may allow the user to register the cushion 104 for use and provide information about the user including a language of the user, a first name of the user, a last name of the user, a phone number of the user, an email address of the user, a serial number of the cushion 104, and a PIN number or a password that allows the user to limit access to the cushion 104. In order for the client computing device 102 to connect to the cushion 104, the user may have to provide the PIN number or the password. After receiving this information from the user, the profile module 216 may store this information in the memory 204 and/or transmit the information to a server computing device using a communication network such as the internet. The server computing device may register the user and transmit registration information to the client computing device 102. Example user interfaces associated with the profile module 216 are shown in FIGS. 4-11.

The inflation application 206 additionally includes a history module 218 that obtains the current immersion at a regular interval, e.g., once a day or multiple times a day, and stores the current immersion in the memory 204. The history module 218 may trigger a reminder that may be a push notification, an email, a text message, or another type of reminder that reminds the user to obtain the current immersion. The current immersion may be obtained automatically or manually. The history module 218 receives the current immersion from the check cushion module 214 and stores the current immersion with previously stored immersion information. The history module 218 may be used to generate a user interface to show the user whether the current immersion level has been appropriate each day over a period of time, such as over the last month. The user may perform gestures on the display 208 to swipe or scroll through the historical immersion level over the period of time. As an example, if the immersion level has been too low in at least one inflation zone, then the history module 218 stores information associated with a low level of inflation in the memory 204. If the immersion level has been too high in at least one inflation zone, then the history module 218 stores information associated with a high level of inflation in the memory 204. If the immersion level has been an appropriate level in at least one inflation zone, then the history module 218 stores information with the appropriate level of inflation in the memory 204.

The history module 218 may collect and store information associated with when the user sets up the cushion initially and each time the user checks the cushion 104.

In a further embodiment, the history module 218 may transmit the information associated with the user of the cushion to the server computing device. The server computer device may store the information in a database associated with the server computer device. This may allow the user to view a history of their cushion checks via a web-based portal and export a history of their cushion checks to a new cushion, among other uses. In another example, the history module 218 may allow the user to share the information associated with the user of the cushion with a caregiver or a clinician, or another recipient. The user may enter an email address and the history module 218 may transmit this information to the caregiver or the clinician. As another example, the user may enter a telephone number and the history module 218 may transmit information as a text message or a multimedia message to the caregiver or the clinician. As another option, the user may export the information into a file such as a comma separated value file, a spreadsheet, or another type of file.

Figure 9:
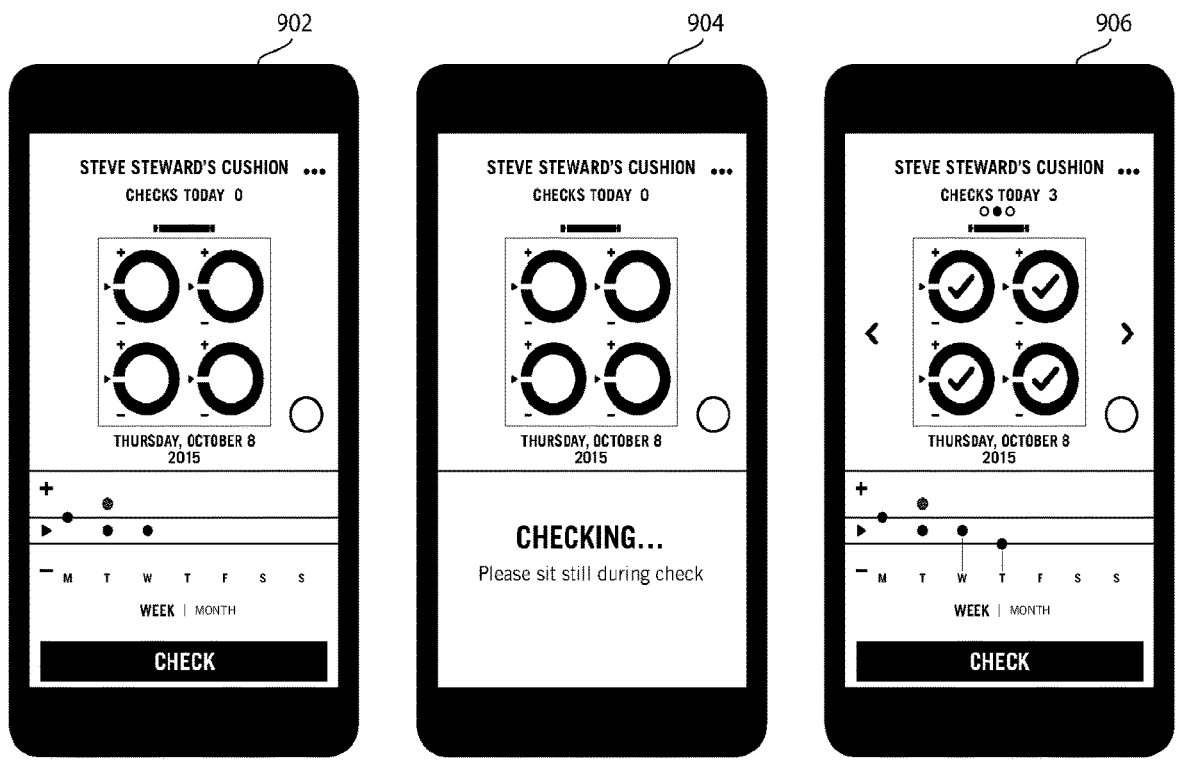
Figure 10:
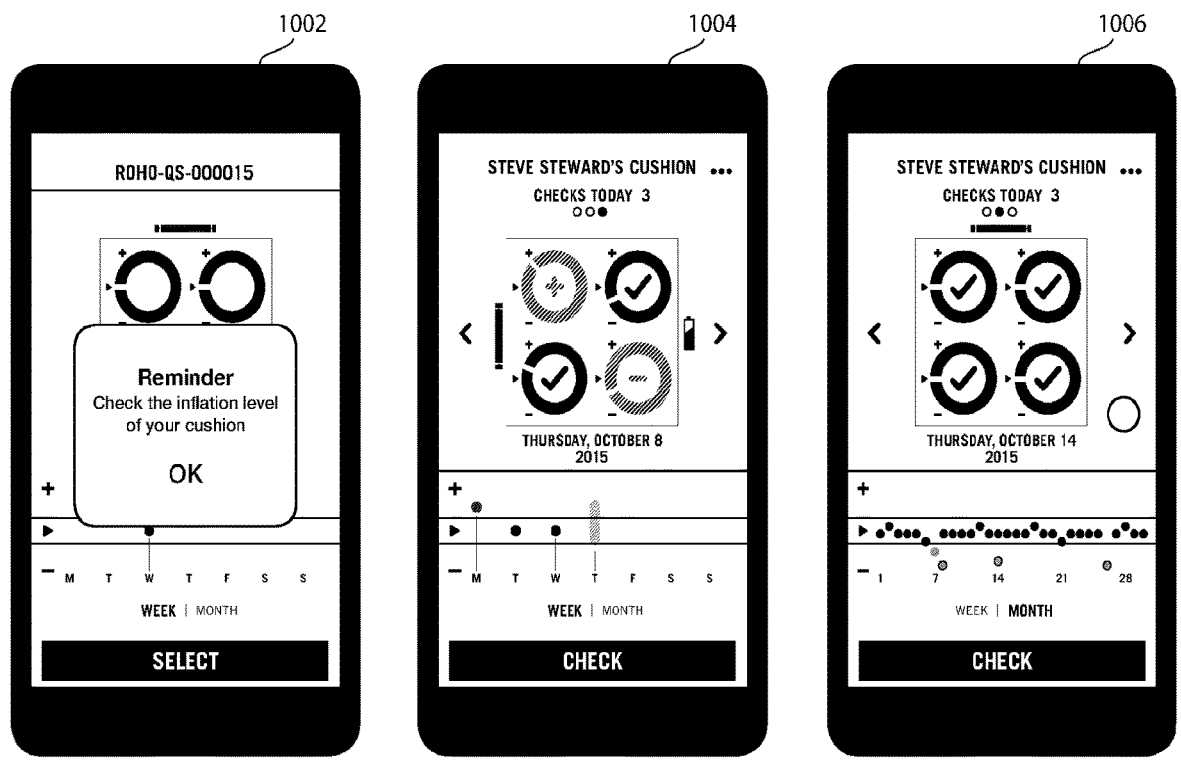

Example user interfaces associated with the history module 218 are shown in FIGS. 9 and 10.

The inflation application 206 also includes a user interface module 220 for displaying a user interface on the display 208. As an example, the user interface module 220 generates a native and/or web-based graphical user interface (GUI) that accepts input and provides output by generating content that is transmitted from the cushion 104 to the client computing device 102 via the communication network 106 and viewed by a user of the client computing device 102. The client computing device 104 may provide real-time automatically and dynamically refreshed information to the user. The user interface module 220 may send data to other modules of the inflation application 206 of the client computing device 102, and retrieve data from other modules of the inflation application 206 of the client computing device 102 asynchronously without interfering with the display and behavior of the user interface displayed by the client computing device 102.

In further embodiments, the profile module 216 or another module of the inflation application 206 may allow a user to set reminder alarms to check the cushion 104 or set reminder alarms to perform a weight shift and/or offload (e.g., pressure relief regime). The setup module 212 of the inflation application 206 may automatically inflate the at least one inflation zone of the cushion 104, automatically deflate the at least one inflation zone of the cushion, and automatically lock individual inflation zones of the cushion. The check cushion module 214 or another module of the inflation application 206 may automatically transmit an alarm that notifies a caregiver if assistance may be needed to fix an over-inflated or under-inflated cushion.

Figure 3:
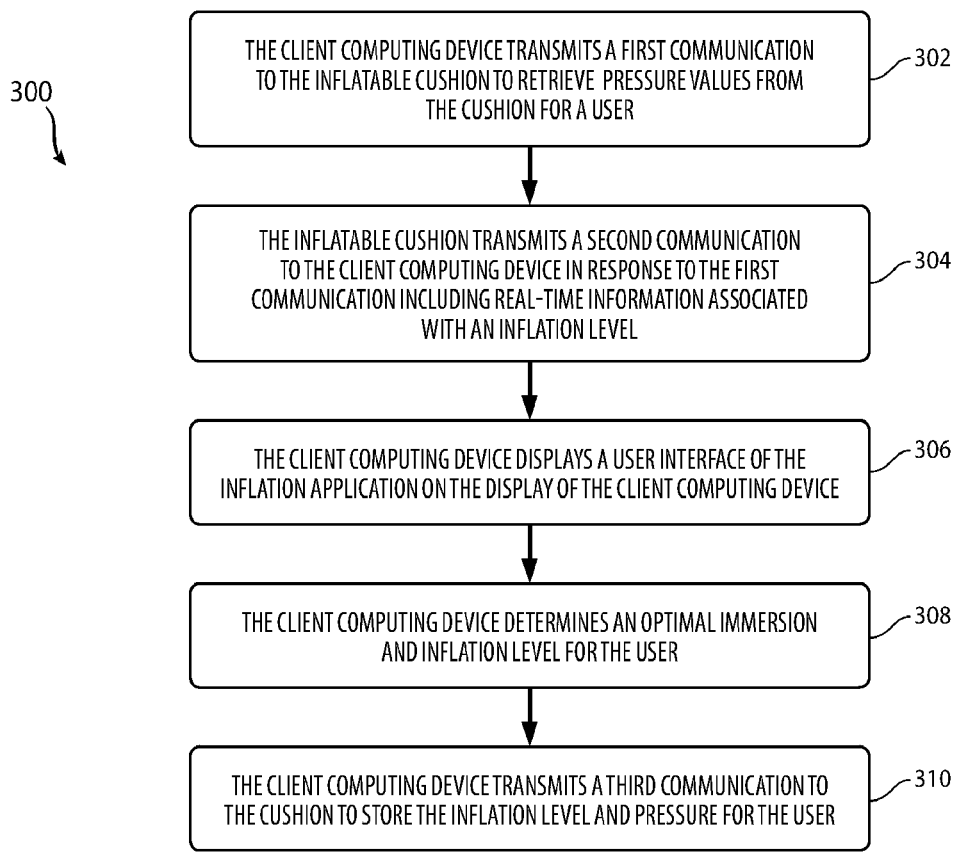
FIG. 3 illustrates a flowchart for inflating a cushion according to an example embodiment.

FIG. 3 illustrates a flowchart of a process 300 executed by the inflation application 306 of the client computing device 102 for optimally inflating the cushion so that the user is optimally immersed in the cushion 104.

At 302, the client computing device 102 transmits a first communication to the hardware device associated with the inflatable cushion 104 to retrieve pressure values from the cushion for a user. The first communication includes instructions to set an inflation level for at least one inflation zone of the cushion. The instructions include a request for pressure value information from the at least one pressure sensor of the cushion so that the setup module 212 can execute the algorithm for detecting optimal immersion of the cushion user into the inflatable cushion.

At 304, the inflatable cushion 104 transmits a second communication to the client computing device 102 in response to the first communication. The client computing device 102 receives the second communication from the inflatable cushion 104. The second communication may include real-time information associated with the inflation level for the at least one inflation zone of the cushion 104.

At 306, the client computing device 102 displays the user interface of the inflation application 206 on the display 208 of the client computing device 102. The user interface may provide the real-time information associated with the inflation level for the at least one inflation zone of the cushion 104. The user interface may be a set up user interface for setting up the cushion for the user, a check cushion user interface, a profile user interface, a history user interface, or another type of user interface.

At 308, the client computing device 102 determines the immersion depth of the user positioned on the cushion by analyzing air pressure in the cushion 104. The setup module 212 accurately determines changes in pressure as air exits the cushion 104, which allows the setup module 212 to determine the optimal internal cushion pressure and the optimal or appropriate inflation level for the user. In an exemplary embodiment, the setup module 212 obtains pressure readings from the cushion 104 at a particular interval, e.g., once per second. The setup module 212 determines an average pressure over a period of N time. As an example, the average pressure may be determined over a period of six to ten seconds. The setup module 212 determines continuous average pressure readings and determines a difference in a current average pressure reading minus the average pressure over the preceding N period of time. When the difference is less than a predetermined value, then the slope of the pressure curve indicates that an optimal pressure representing ideal or optimal immersion for the user has been reached. A representation of the optimal pressure may be displayed to the user on the display 208 of the client computing device 102.

At 310, the client computing device 102 transmits a third communication to the cushion 104 to store the inflation level and pressure for the at least one inflation zone of the cushion for the user after determining the appropriate inflation level for the at least one inflation zone of the cushion 104. The cushion 104 stores the appropriate inflation level and/or pressure in its memory and/or the client computing device 102 stores the appropriate inflation level and/or pressure in the memory 204. For a cushion having more than one inflation zone or section, the user may adjust the air pressure and lock air in the separate sections. After the air is locked in the separate sections, the cushion 104 stores the locked air pressure level in its memory and/or the client computing device 102 stores the locked air pressure level in the memory 204.

After the cushion has been set at the appropriate inflation level for the at least one inflation zone, the cushion 104 is ready for use by the user. In addition, the client computing device 102 may check the cushion 104 automatically or at the request of the user. When the client computing device 102 checks the cushion, the client computing device and/or the cushion 104 compares a current inflation level for the at least one inflation zone with the appropriate inflation level for the at least one inflation zone. The client computing device 102 may store information associated with the comparison in the memory 204 and display information associated with the comparison on the display 208. In addition, if the current inflation level does not match the appropriate inflation level for the at least one inflation zone, the client computing device 102 and/or the cushion may adjust the current inflation level for the at least one inflation zone to be the appropriate inflation level for the at least one inflation zone. Additionally, the client computing device 102 and/or the cushion 104 may provide a notification that indicates that the current inflation level does not match the appropriate inflation level for the at least one inflation zone. The notification may be at least one of a visual notification, an audible notification, and a haptic notification, such as a vibration.

According to an embodiment, the client computing device 102 may be used to setup and set the appropriate inflation level for more than one cushion 104. The client computing device 102 may perform the process 300 each time to setup and set the appropriate inflation level for each cushion. The client computing device 102 transmits a fourth communication to the hardware device associated with a second inflatable cushion 104 to retrieve pressure values from the cushion for a user. The fourth communication is similar to the first communication described above. Next, the second inflatable cushion 104 transmits a fifth communication to the client computing device 102 in response to the fourth communication. The client computing device 102 receives the fifth communication from the second inflatable cushion 104. The fifth communication may include real-time information associated with the inflation level for the at least one inflation zone of the second cushion 104. The client computing device 102 displays the user interface of the inflation application 206 on the display 208 of the client computing device 102. Next, the client computing device 102 determines the immersion depth of the user positioned on the second cushion by analyzing air pressure in the second cushion 104. The client computing device 102 transmits a sixth communication to the second cushion 104 to store the inflation level and pressure for the at least one inflation zone of the second cushion for the user after determining the appropriate inflation level for the at least one inflation zone of the second cushion 104. The second cushion 104 stores the appropriate inflation level and/or pressure in its memory and/or the client computing device 102 stores the appropriate inflation level and/or pressure in the memory 204.

Figure 4:
FIGS. 4-11 illustrate screenshots of a user interface of an inflation application according to example embodiments.

FIG. 4 illustrates three screenshots of the inflation application 206 according to an example embodiment. FIG. 4 shows a first user interface 402 for the inflation application 206 that provides a splash screen of the inflation application 206 that is displayed when the client computing device 102 launches the inflation application 206 and/or at another time. FIG. 4 shows a second user interface 404 that displays a registration user interface for registering to use the inflation application 206 by providing an email address. A representation of the email address may be stored in the database associated with the server computing device described herein. FIG. 4 provides a third user interface 406 to select the cushion 104 and connecting to the cushion via Bluetooth with the client computing device 102.

Figure 5:
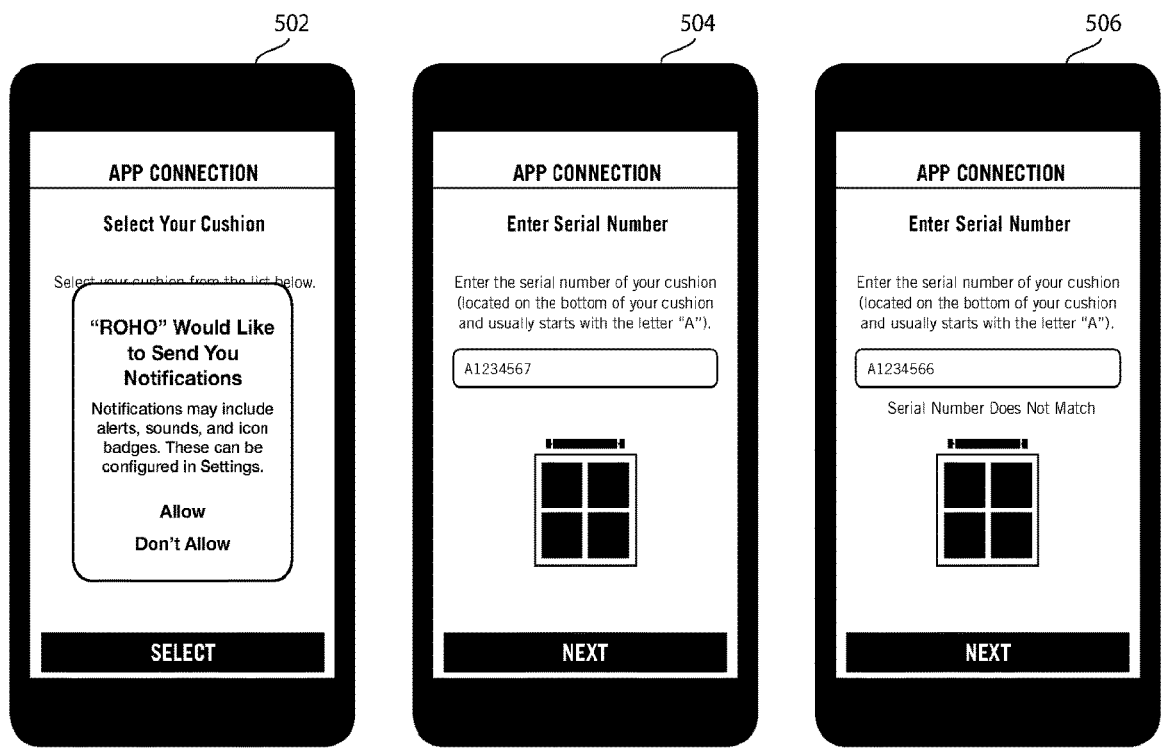

FIG. 5 illustrates three screenshots of the inflation application 206 according to an example embodiment. FIG. 5 illustrates a first user interface 502 that shows a modal notification that provides the user with the ability to allow or disallow the inflation application 206 to send notifications including alerts, sounds, and icon badges. As shown on the first user interface, this may be configured or changed in application settings. FIG. 5 shows a second user interface 504 that allows the user to enter the serial number of the cushion 104. FIG. 5 shows a third user interface 506 that displays an error message indicating that the user entered an incorrect serial number. This provides a security feature that prevents an unauthorized user from connecting to a cushion. If an incorrect serial number is entered, the client computing device 102 is not connected to the cushion 104. The user is requested to reenter the serial number to connect the client computing device 102 with the cushion 104.

Figure 6:
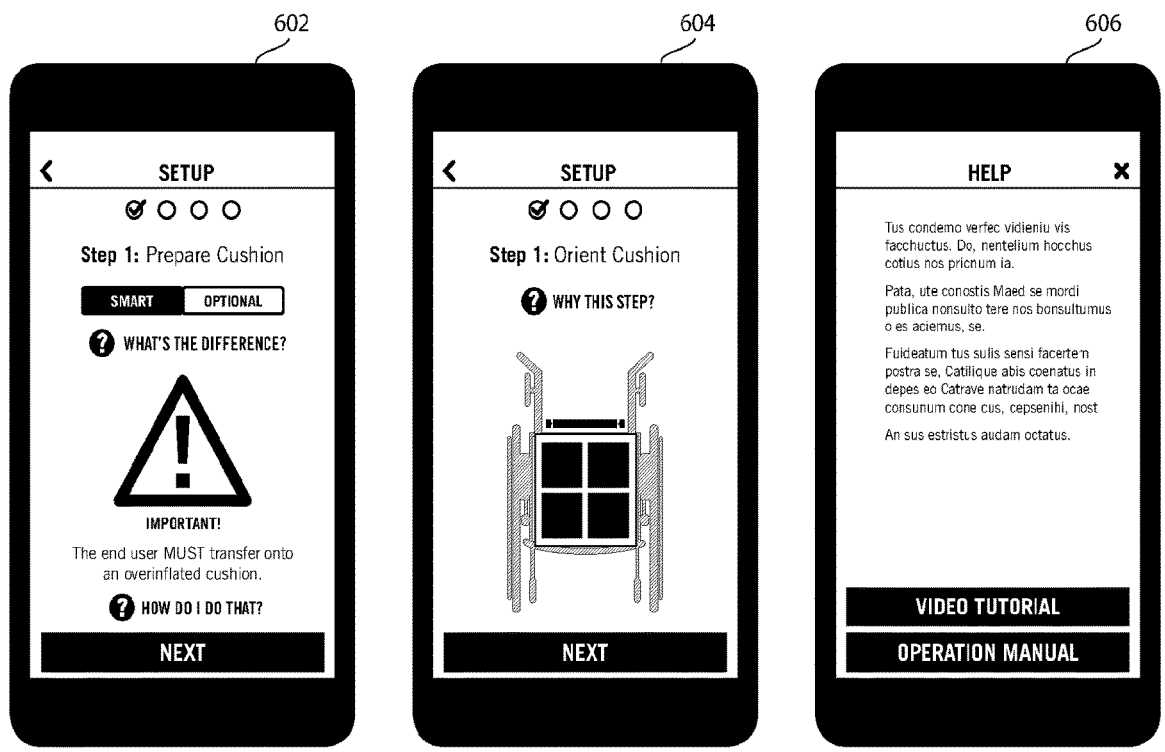

FIG. 6 illustrates three screenshots of the inflation application 206 according to an example embodiment. FIG. 6 illustrates a first user interface 602 that displays a first set up user interface that indicates that the user should prepare the cushion for use. As shown, the user is instructed to transfer onto an overinflated cushion. FIG. 6 illustrates a second user interface 604 that displays the first set up user interface for setting up the cushion 104 for use by the user. This user interface displays a graphic that indicates how the cushion should be oriented on a seat. FIG. 6 illustrates a third user interface 606 that is a help user interface that provides help text, a button for playing a video tutorial associated with the system, and a button for displaying an operation manual associated with the system 100.

Figure 7:
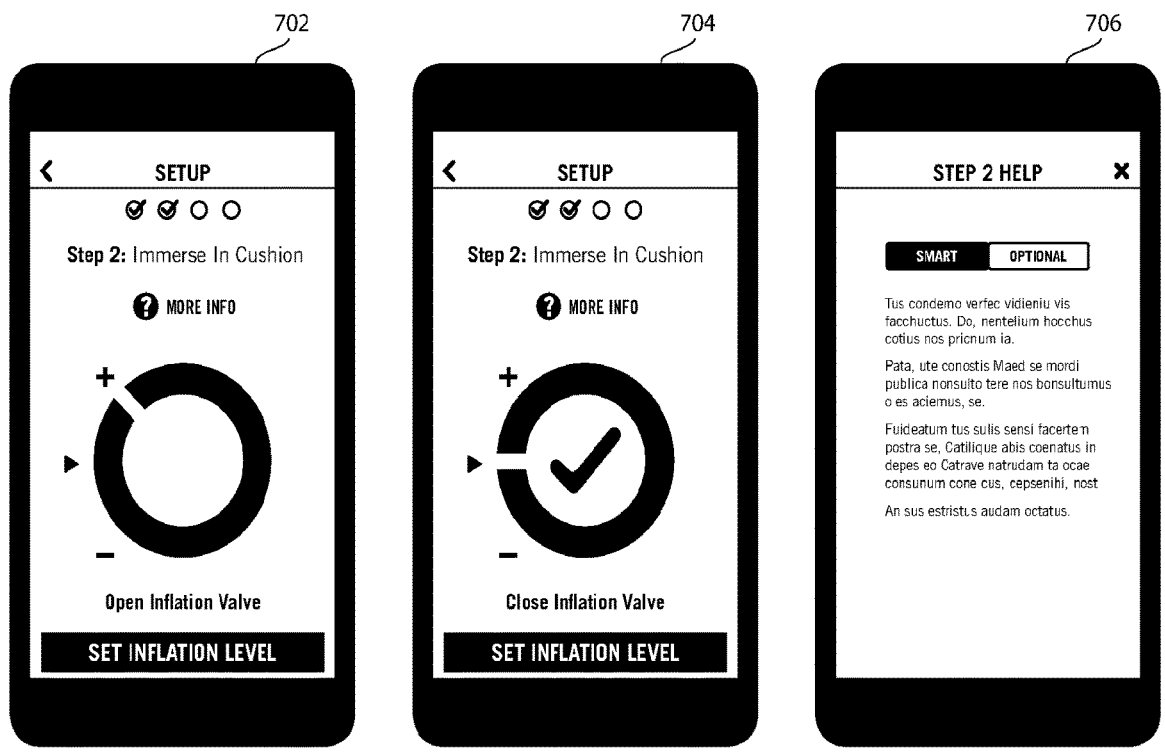

FIG. 7 illustrates a first user interface 702 that displays a second set up user interface for setting an inflation level of the cushion 104 and instructs the user to immerse in the cushion 104.

When setting the inflation level of the cushion 104, the user may manually fill the cushion 104 with air. The user may then open the inflation valve and let air escape from the cushion while immersing into the cushion. Initially, the user interface may display an indicator that shows that the cushion is over inflated. The indicator may be red and may be "+". The indicator also may instruct the user to open the inflation valve. When the user does this, the indicator may show a circle that rotates counter clockwise or in another manner as the air exits the cushion. When enough air has exited the cushion, the cushion may determine that the appropriate pressure has been reached. The indicator may be a green check mark or another type of indicator that indicates that it is time to close the inflation valve.

The second set up user interface includes a button that when selected begins to set an inflation level for the cushion 104. As the cushion is being filled with air, the user interface may display an indicator that indicates that the cushion is being filled. The indicator may be a first color such as red. FIG. 7 shows a second user interface 704 that displays a user interface for setting the inflation level of the cushion 104. This user interface displays another indicator that indicates that the cushion has been filled with air to an appropriate inflation level. This indicator may be a second color such as green and may include a check mark that indicates that the cushion has reached the appropriate inflation level.

While the cushion is being inflated or deflated, the indicator, shown as a circle may rotate in real-time based on the slope of the pressure curve as shown in FIG. 2B. Additionally, the rotation of the circle may be based on the inflation level. The rotation may be clockwise/counterclockwise when the cushion is in the process of inflation and counterclockwise/clockwise when the cushion is in the process of deflation. In addition, the color of the indicator may be based on the slope and based on the inflation level. As shown in the first user interface, the indicator includes a center notch that is pointing toward "+". As shown in the second user interface, the center notch is pointing toward a triangle that is associated with the appropriate inflation level. As air is released from the cushion and the user immerses into the cushion, the center notch may rotate toward the triangle. In addition, the color of the circle may change from red, to yellow, and then to green as the center notch rotates toward the triangle.

According to an embodiment, the client application 206 may execute one of a smart setup mode and a manual setup mode. The setup described above and shown in screenshots refers to the smart setup mode. In the manual setup mode, the user may perform a traditional hand check to determine whether the cushion 104 is appropriately inflated. After performing the traditional hand check, the user may store the manually established at least one inflation level of the at least one inflation zone of the cushion 104 in the memory 204 of the client computing device 102 and/or the memory of the cushion 104.

FIG. 7 shows a third user interface 706 that is a help user interface for setting up the cushion 104.

Figure 8:

FIG. 8 illustrates two screenshots of the inflation application 206 according to an example embodiment. FIG. 8 illustrates a first user interface 802 that displays an adjust and lock user interface that allows a user to adjust the at least one inflation zone of the cushion 104, lock the inflation level for the at least one inflation zone, and save the inflation level in memory of the cushion 104 and/or memory 204 of the client computing device 102. FIG. 8 illustrates a second user interface 804 that displays a set up complete user interface that indicates that the cushion is properly configured and includes a "Done" button for exiting the set up process. FIG. 9 illustrates three screenshots of the inflation application 206 according to an example embodiment. FIG. 9 illustrates three different user screenshots that each provides a check cushion interface. In a first check cushion user interface 902, the user interface shows N different inflation zone indicators in a first portion of the user interface and a check cushion calendar/history log in a second portion of the user interface that indicates historical information associated with checking the cushion. Although there are four inflation zone indicators shown in FIG. 9, there could be more or fewer than four. The four different inflation zone indicators may each rotate based on air pressure in a respective inflation zone. In addition, the four different inflation zone indicators may have a color that is based on the air pressure in the respective inflation zone. In the check cushion calendar/history log, each dot may be based on an average pressure of the cushion. In addition, the color of the dot (green/yellow/red) may be based on the average pressure of the cushion.

In a second check cushion user interface 904, the user interface shows that the cushion 104 and the client computing device 102 are in the process of checking the inflation level of the cushion 104. In a third user check cushion user interface 906, the user interface shows four different inflation zone indicators in a first portion of the user interface and a check cushion calendar in a second portion of the user interface. As shown in this third check cushion user interface, the four inflation zones have an appropriate inflation level on Thursday, Oct. 8, 2015 and there have been three checks made on this date.

As shown in the third check cushion user interface, a first center notch on the top left indicates that the first inflation zone is slightly overinflated, but still appropriately inflated. Thus, there is still a check mark. A second center notch on the top right indicates that the second inflation zone is appropriately inflated. A third center notch on the bottom left indicates that the third inflation zone is appropriately inflated. A fourth center notch on the bottom right indicates that the fourth inflation zone is slightly underinflated, but still appropriately inflated. Thus, there is a check mark. The first, second, third, and fourth inflation zones are appropriately inflated. The user may make a gesture and swipe or horizontally scroll between checks conducted on this date using the first portion of the user interface and view the four different inflation zone indicators for each check.

FIG. 10 illustrates three screenshots of the inflation application 206 according to an example embodiment. FIG. 10 illustrates three different user interfaces that are each a check cushion user interface. In a first check cushion user interface 1002, the user interface displays a reminder that requests that the user check the inflation level of the cushion. This reminder may be provided at a regular interval of time such as once a day at a particular time or multiple times a day. The reminder is a modal dialog box that includes an "OK" button that is displayed above the check cushion user interface. Once the user selects the "OK" button, the user can begin to check the inflation levels of the inflation zones of the cushion 104. In a second check cushion user interface 1004, the user interface shows four different inflation zone indicators in a first portion of the user interface and a check cushion calendar in a second portion of the user interface. As shown in this user interface, two of the inflation zones have an appropriate inflation level. However, the top left indicator shows that the respective inflation zone is overinflated and the bottom right indicator shows that the respective inflation zone is underinflated. The indicators may be different colors such as yellow or red to indicate that the user is not at an optimal inflation level. Alternatively, the indicators may be "+" or "−" to indicate that the user is not at an optimal inflation level and the cushion is over inflated or under inflated.

In a third check cushion user interface 1006, the user interface shows four different inflation zone indicators in a first portion of the user interface and a check cushion calendar in a second portion of the user interface. As shown in this user interface, the four inflation zones have an appropriate inflation level on Thursday, Oct. 14, 2015 and there have been three checks made on this date. In addition, the check cushion calendar shows the history of checks made over the last month.

Figure 11:
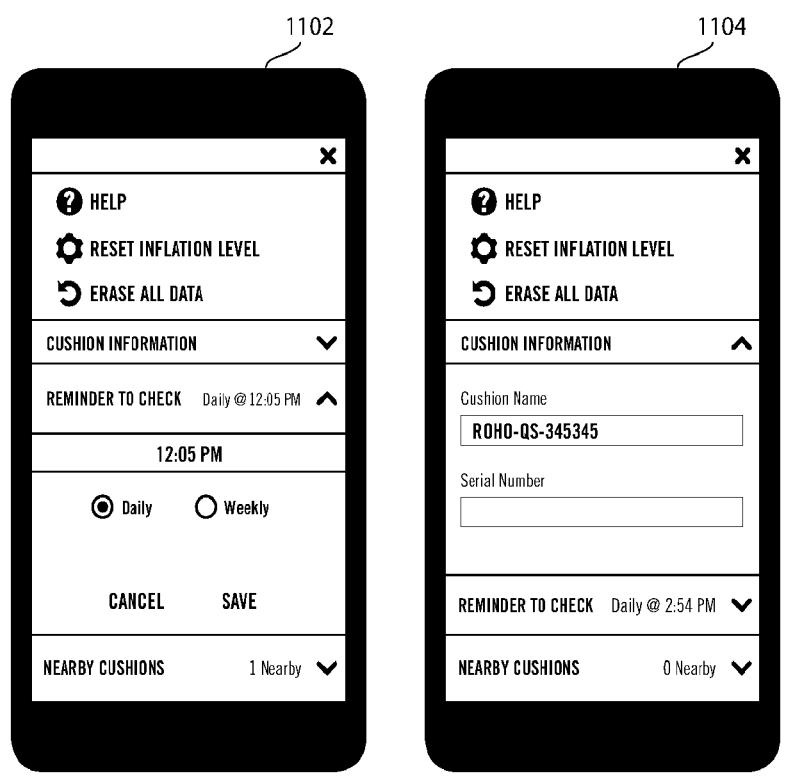

FIG. 11 illustrates two screenshots of the inflation application 206 according to an example embodiment. FIG. 11 shows two different user interfaces that provide a settings user interface. In a first settings user interface 1102, the user interface shows a Help button, a Reset Inflation Level button, an Erase All Data button, a collapsible Cushion Information section, a Reminder to Check collapsible section, and a Nearby Cushions collapsible section. In the first settings user interface 1102, the Reminder to Check section is expanded to show that the user has set a reminder to check to occur daily at 12:05 pm. The Cushion Information section is collapsed and the Nearby Cushions section is collapsed but shows that there is one nearby cushion. In a second settings user interface 1104, the user interface is similar to the first settings user interface. However, it shows that the Cushion Information section is expanded to show the cushion name and a blank serial number field. In addition, the Reminder to Check section is collapsed but shows that the user has set a reminder to check to occur daily at 2:54 pm. In addition, the Nearby Cushions section is collapsed but shows that there are no nearby cushions.

Figure 12:
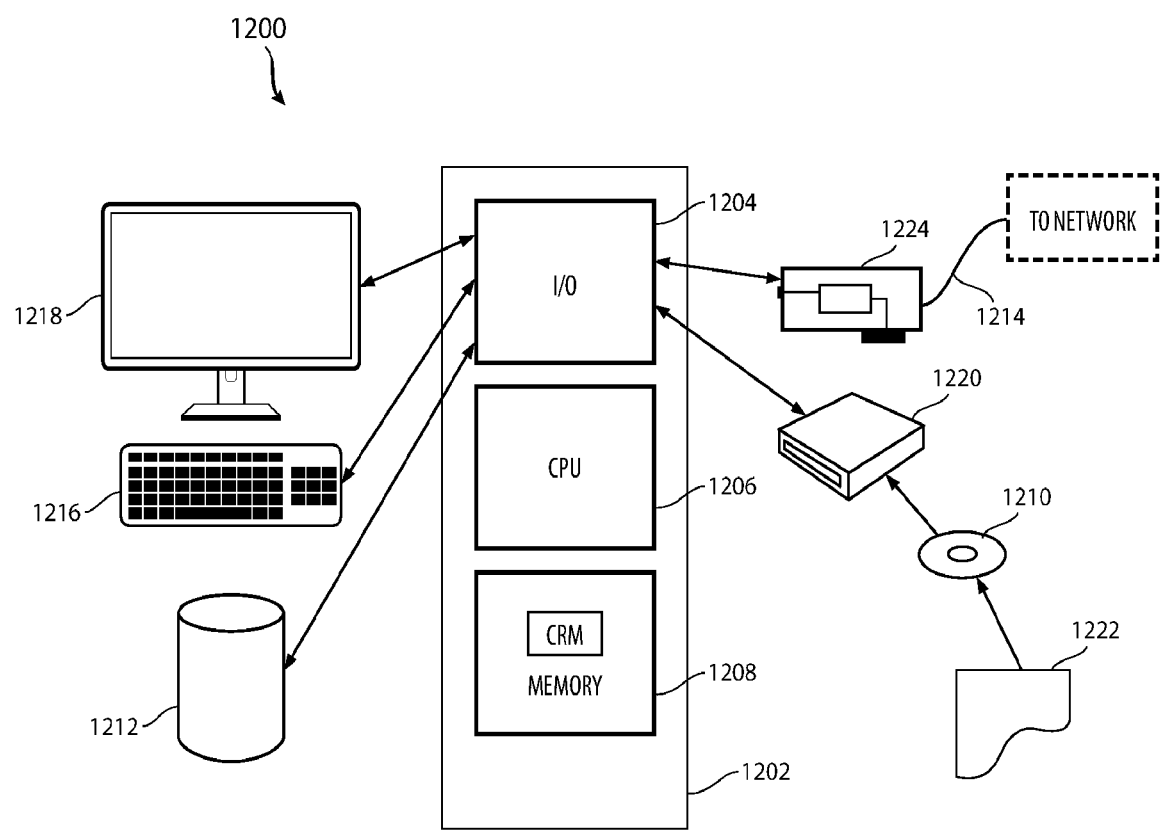
FIG. 12 illustrates a block diagram of an example computer device for use with the example embodiments.

FIG. 12 illustrates an example computing system 1200 that may implement various systems, such as the client computing device 102 and the cushion 104, and the methods discussed herein, such as process 300. A general purpose computer system 1200 is capable of executing a computer program product to execute a computer process. Data and program files may be input to the computer system 1200, which reads the files and executes the programs therein such as the inflation application 206. Some of the elements of a general purpose computer system 1200 are shown in FIG. 12 wherein a processor 1202 is shown having an input/output (I/O) section 1204, a central processing unit (CPU) 1206, and a memory section 1208. There may be one or more processors 1202, such that the processor 1202 of the computer system 1200 comprises a single central-processing unit 1206, or a plurality of processing units, commonly referred to as a parallel processing environment. The computer system 1200 may be a conventional computer, a server, a distributed computer, or any other type of computer, such as one or more external computers made available via a cloud computing architecture. The presently described technology is optionally implemented in software devices loaded in memory 1208, stored on a configured DVD/CD-ROM 1210 or storage unit 1212, and/or communicated via a wired or wireless network link 1214, thereby transforming the computer system 1200 in FIG. 12 to a special purpose machine for implementing the described operations.

The memory section 1208 may be volatile media, non-volatile media, removable media, non-removable media, and/or other media or mediums that can be accessed by a general purpose or special purpose computing device. For example, the memory section 1208 may include non-transitory computer storage media and communication media. Non-transitory computer storage media further may include volatile, nonvolatile, removable, and/or non-removable media implemented in a method or technology for the storage (and retrieval) of information, such as computer/machine-readable/executable instructions, data and data structures, engines, program modules, and/or other data. Communication media may, for example, embody computer/machine-readable/executable, data structures, program modules, algorithms, and/or other data. The communication media may also include an information delivery technology. The communication media may include wired and/or wireless connections and technologies and be used to transmit and/or receive wired and/or wireless communications.

The I/O section 1204 is connected to one or more user-interface devices (e.g., a keyboard 1216 and a display unit 1218), a disc storage unit 1212, and a disc drive unit 1220. Generally, the disc drive unit 1220 is a DVD/CD-ROM drive unit capable of reading the DVD/CD-ROM medium 1210, which typically contains programs and data 1222. Computer program products containing mechanisms to effectuate the systems and methods in accordance with the presently described technology may reside in the memory section 1204, on a disc storage unit 1212, on the DVD/CD-ROM medium 1210 of the computer system 1200, or on external storage devices made available via a cloud computing architecture with such computer program products, including one or more database management products, web server products, application server products, and/or other additional software components. Alternatively, a disc drive unit 1220 may be replaced or supplemented by a floppy drive unit, a tape drive unit, or other storage medium drive unit. The network adapter 1224 is capable of connecting the computer system 1200 to a network via the network link 1214, through which the computer system can receive instructions and data. Examples of such systems include personal computers, Intel or PowerPC-based computing systems, AMD-based computing systems, ARM-based computing systems, and other systems running a Windows-based, a UNIX-based, or other operating system. It should be understood that computing systems may also embody devices such as Personal Digital Assistants (PDAs), mobile phones, tablets or slates, multimedia consoles, gaming consoles, set top boxes, etc.

When used in a LAN-networking environment, the computer system 1000 is connected (by wired connection and/or wirelessly) to a local network through the network interface or adapter 1224, which is one type of communications device. When used in a WAN-networking environment, the computer system 1200 typically includes a modem, a network adapter, or any other type of communications device for establishing communications over the wide area network. In a networked environment, program modules depicted relative to the computer system 1200 or portions thereof, may be stored in a remote memory storage device. It is appreciated that the network connections shown are examples of communications devices for and other means of establishing a communications link between the computers may be used.

In an example implementation, source code executed by the client computing device 102 and the cushion 104, a plurality of internal and external databases, source databases, and/or cached data on servers are stored in the memory 204 of the client computing device 102, memory of the cushion 104, or other storage systems, such as the disk storage unit 1212 or the DVD/CD-ROM medium 1210, and/or other external storage devices made available and accessible via a network architecture. The source code executed by the client computing device 102 and the cushion 104 may be embodied by instructions stored on such storage systems and executed by the processor 1202.

Some or all of the operations described herein may be performed by the processor 1202, which is hardware. Further, local computing systems, remote data sources and/or services, and other associated logic represent firmware, hardware, and/or software configured to control operations of the inflation system 100 and/or other components. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 1202 and a user may interact with a Graphical User Interface (GUI) using one or more user-interface devices (e.g., the keyboard 1216, the display unit 1218, and the user devices 1204) with some of the data in use directly coming from online sources and data stores. The system set forth in FIG. 12 is but one possible example of a computer system that may employ or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon executable instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic executable instructions.

The description above includes example systems, methods, techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:
1. A method comprising:
transmitting, from a remote computing device, a first communication to a hardware device associated with an inflatable cushion to configure the cushion, the first communication comprising a request for an inflation level for at least one inflation zone of the cushion;

receiving, by the remote computing device, a second communication from the hardware device associated with the inflatable cushion, the second communication comprising real-time information associated with the inflation level for the at least one inflation zone of the cushion;

displaying on a user interface associated with the remote computing device the real-time information associated with the inflation level for the at least one inflation zone of the cushion;

determining, by the remote computing device, an appropriate inflation level for the at least one inflation zone of the cushion by executing instructions to set the appropriate inflation level for the at least one inflation zone of the cushion and using the real-time information associated with the inflation level for the at least one inflation zone of the cushion provided in the second communication, the instructions to set the appropriate inflation level for the at least one inflation zone of the cushion comprise determining a current average air pressure level within the cushion at a particular time interval over a period of N time, determining a preceding average air pressure level over an immediately preceding period of N time, determining a difference between the current average air pressure level and the preceding average air pressure level, and determining that an appropriate inflation level for optimal immersion has been reached when the difference is less than a predetermined value; and transmitting, from the remote computing device, a third communication to the hardware device to store the appropriate inflation level for the at least one inflation zone of the cushion.

2. The method of claim 1, wherein the hardware device associated with the inflatable cushion comprises a first Bluetooth Low Energy (BLE) hardware device.

3. The method of claim 2, further comprising transmitting the instructions to set the appropriate inflation level for the at least one inflation zone of the cushion from a second BLE hardware device to the first BLE hardware device.

4. The method of claim 1, further comprising storing the appropriate inflation level for the at least one inflation zone of the cushion in a memory of the remote computing device, transmitting the appropriate inflation level for the at least one inflation zone of the cushion to the hardware device of the cushion, and storing the appropriate inflation level for the at least one inflation zone of the cushion in a memory of the hardware device of the cushion.

5. The method of claim 4, further comprising transmitting from the remote computing device a communication requesting a state of the cushion, receiving by the remote computing device a current inflation level for the at least one inflation zone of the cushion, comparing by the remote computing device the appropriate inflation level for the at least one inflation zone of the cushion with the current inflation level for the at least one inflation zone of the cushion, and displaying on the user interface of the remote computing device comparison information that indicates whether there is a difference between the appropriate inflation level for the at least one inflation zone of the cushion with the current inflation level for the at least one inflation zone of the cushion.

6. The method of claim 5, further comprising storing a representation of the comparison information that indicates whether there is the difference between the appropriate inflation level for the at least one inflation zone of the cushion with the current inflation level for the at least one inflation zone of the cushion in the memory of the hardware device of the cushion.

7. The method of claim 1, further comprising displaying on the user interface the real-time information associated with the inflation level for each inflation zone of the cushion.

8. The method of claim 1, wherein the inflatable cushion is a first inflatable cushion, the method further comprising:

transmitting, from the remote computing device, a fourth communication to a hardware device associated with a second inflatable cushion to configure the second inflatable cushion, the fourth communication comprising a request for an inflation level for at least one inflation zone of the second inflatable cushion;

receiving, by the remote computing device, a fifth communication from the hardware device associated with the second inflatable cushion, the fifth communication comprising real-time information associated with the inflation level for the at least one inflation zone of the second inflatable cushion;

displaying on the user interface associated with the remote computing device the real-time information associated with the inflation level for the at least one inflation zone of the second inflatable cushion;

determining, by the remote computing device, an appropriate inflation level for the at least one inflation zone of the second inflatable cushion by executing instructions to set the appropriate inflation level for the at least one inflation zone of the second inflatable cushion and using the real-time information associated with the inflation level for the at least one inflation zone of the second inflatable cushion provided in the fifth communication, the instructions to set the appropriate inflation level comprise determining a current average air pressure level within the second inflatable cushion at a particular time interval over a period of N time, determining a preceding average air pressure level over an immediately preceding period of N time, determining a difference between the current average air pressure level and the preceding average air pressure level, and determining that an appropriate inflation level for optimal immersion has been reached when the difference is less than a predetermined value; and transmitting, from the remote computing device, a sixth communication to the hardware device associated with the second inflatable cushion to store the appropriate inflation level for the at least one inflation zone of the second inflatable cushion.

9. A non-transitory computer-readable medium having instructions stored thereon that, when executed by at least one processor, cause the at least one processor to perform operations comprising:

transmitting a first communication to a hardware device associated with an inflatable cushion to configure the cushion, the first communication comprising a request for an inflation level for at least one inflation zone of the cushion;

receiving a second communication from the hardware device associated with the inflatable cushion, the second communication comprising real-time information associated with the inflation level for the at least one inflation zone of the cushion;

displaying on a user interface the real-time information associated with the inflation level for the at least one inflation zone of the cushion;

determining an appropriate inflation level for the at least one inflation zone of the cushion by executing instructions to set the appropriate inflation level for the at least one inflation zone of the cushion using the real-time information associated with the inflation level for the at least one inflation zone of the cushion provided in the second communication, wherein the instructions to set the appropriate inflation level comprises determining a current average air pressure level within the cushion at a particular time interval over a period of N time, determining a preceding average air pressure level over an immediately preceding period of N time, determining a difference between the current average air pressure level and the preceding average air pressure level, and determining that an appropriate inflation level for optimal immersion has been reached when the difference is less than a predetermined value; and transmitting a third communication to the hardware device to store the appropriate inflation level for the at least one inflation zone of the cushion.

10. The non-transitory computer-readable medium of claim 9, wherein the hardware device associated with the inflatable cushion comprises a first Bluetooth Low Energy (BLE) hardware device.

11. The non-transitory computer-readable medium of claim 10, the operations further comprising transmitting the instructions to set the appropriate inflation level for the at least one inflation zone of the cushion from a second BLE hardware device to the first BLE hardware device.

12. The non-transitory computer-readable medium of claim 9, the operations further comprising storing the appropriate inflation level for the at least one inflation zone of the cushion in a memory associated with the at least one processor, transmitting the appropriate inflation level for the at least one inflation zone of the cushion to the hardware device of the cushion, and storing the appropriate inflation level for the at least one inflation zone of the cushion in a memory of the hardware device of the cushion.

13. The non-transitory computer-readable medium of claim 12, the operations further comprising transmitting a communication requesting a state of the cushion, receiving a current inflation level for the at least one inflation zone of the cushion, comparing the appropriate inflation level for the at least one inflation zone of the cushion with the current inflation level for the at least one inflation zone of the cushion, and displaying on the user interface comparison information that indicates whether there is a difference between the appropriate inflation level for the at least one inflation zone of the cushion with the current inflation level for the at least one inflation zone of the cushion.

14. The non-transitory computer-readable medium of claim 13, the operations further comprising storing a representation of the comparison information that indicates whether there is the difference between the appropriate inflation level for the at least one inflation zone of the cushion with the current inflation level for the at least one inflation zone of the cushion in the memory associated with the at least one processor.

15. The non-transitory computer-readable medium of claim 9, the operations further comprising displaying a user interface element that indicates the real-time information associated with the inflation level for each inflation zone of the cushion.

16. The non-transitory computer-readable medium of claim 9, wherein the inflatable cushion is a first inflatable cushion, the operations further comprising:

transmitting a fourth communication to a hardware device associated with a second inflatable cushion to configure the second inflatable cushion, the fourth communication comprising a request for an inflation level for at least one inflation zone of the second inflatable cushion;

receiving a fifth communication from the hardware device associated with the second inflatable cushion, the fifth communication comprising real-time information associated with the inflation level for the at least one inflation zone of the second inflatable cushion;

displaying on the user interface the real-time information associated with the inflation level for the at least one inflation zone of the second inflatable cushion;

determining an appropriate inflation level for the at least one inflation zone of the second inflatable cushion by executing instructions to set the appropriate inflation level for the at least one inflation zone of the second cushion using the real-time information associated with the inflation level for the at least one inflation zone of the second cushion provided in the fifth communication, wherein the instructions to set the appropriate inflation level comprises determining a current average air pressure level within the cushion at a particular time interval over a period of N time, determining a preceding average air pressure level over an immediately preceding period of N time, determining a difference between the current average air pressure level and the preceding average air pressure level, and determining that an appropriate inflation level for optimal immersion has been reached when the difference is less than a predetermined value; and transmitting a sixth communication to the hardware device associated with the second inflatable cushion to store the appropriate inflation level for the at least one inflation zone of the second inflatable cushion.

17. A system comprising:

a remote computing device including:
  a user interface;
  a memory; and
  at least one processor configured to:
    transmit a first communication to a hardware device associated with an inflatable cushion to configure the cushion, the first communication comprising a request for an inflation level for at least one inflation zone of the cushion;
    receive a second communication from the hardware device associated with the inflatable cushion, the second communication comprising real-time information associated with the inflation level for the at least one inflation zone of the cushion;
    display on the user interface the real-time information associated with the inflation level for the at least one inflation zone of the cushion;
    determine an appropriate inflation level for the at least one inflation zone of the cushion based on the second communication, wherein determining the appropriate inflation level comprises determining a current average air pressure level within the cushion at a particular time interval over a period of N time, determining a preceding average air pressure level over an immediately preceding period of N time, determining a difference between the current average air pressure level and the preceding average air pressure level, and determining that an appropriate inflation level for optimal immersion has been reached when the difference is less than a predetermined value; and transmit a third communication to the hardware device to store the appropriate inflation level for the at least one inflation zone of the cushion.

18. The system of claim 17, wherein the hardware device associated with the inflatable cushion comprises a first Bluetooth Low Energy (BLE) hardware device.

19. The system of claim 18, further comprising a second BLE hardware device that communicates with the first BLE hardware device.

20. The system of claim 17, the at least one processor further configured to store the appropriate inflation level for the at least one inflation zone of the cushion in the memory, transmit the appropriate inflation level for the at least one inflation zone of the cushion to the hardware device of the cushion, and store the appropriate inflation level for the at least one inflation zone of the cushion in a memory of the hardware device of the cushion.

21. The system of claim 20, the at least one processor further configured to transmit a communication requesting a state of the cushion, receive a current inflation level for the at least one inflation zone of the cushion, compare the appropriate inflation level for the at least one inflation zone of the cushion with the current inflation level for the at least one inflation zone of the cushion, and display on the user interface comparison information that indicates whether there is a difference between the appropriate inflation level for the at least one inflation zone of the cushion with the current inflation level for the at least one inflation zone of the cushion.

22. The system of claim 21, the at least one processor further configured to store a representation of the comparison information that indicates whether there is the difference between the appropriate inflation level for the at least one inflation zone of the cushion with the current inflation level for the at least one inflation zone of the cushion in the memory of the remote computing device.

23. The system of claim 17, the at least one processor further configured to display a user interface element that indicates the real-time information associated with the inflation level for each inflation zone of the cushion.

24. The system of claim 17, wherein the inflatable cushion is a first inflatable cushion, the at least one processor further configured to:
transmit a fourth communication to a hardware device associated with a second inflatable cushion to configure the second inflatable cushion, the fourth communication comprising a request for an inflation level for at least one inflation zone of the second inflatable cushion;
receive a fifth communication from the hardware device associated with the second inflatable cushion, the fifth communication comprising real-time information associated with the inflation level for the at least one inflation zone of the second inflatable cushion;
display on the user interface the real-time information associated with the inflation level for the at least one inflation zone of the second inflatable cushion;
determine an appropriate inflation level for the at least one inflation zone of the second inflatable cushion based on the fifth communication, wherein determining the appropriate inflation level comprises determining a current average air pressure level within the second inflatable cushion at a particular time interval over a period of N time, determining a preceding average air pressure level over an immediately preceding period of N time, determining a difference between the current average air pressure level and the preceding average air pressure level, and determining that an appropriate inflation level for optimal immersion has been reached when the difference is less than a predetermined value; and
transmit a sixth communication to the hardware device associated with the second inflatable cushion to store the appropriate inflation level for the at least one inflation zone of the second inflatable cushion.

\* \* \* \* \*